United States Patent [19]

Burdick et al.

[11] Patent Number: 5,171,669
[45] Date of Patent: Dec. 15, 1992

[54] COBALT(III) REAGENTS IN COMBINATION WITH WATER SOLUBLE POLYMERS

[75] Inventors: Brent A. Burdick; Robert W. Zercie, both of Rochester, N.Y.

[73] Assignee: Eastman Kodak Company, Rochester, N.Y.

[21] Appl. No.: 45,937

[22] Filed: May 4, 1987

[51] Int. Cl.$^5$ .............................................. C12Q 1/02
[52] U.S. Cl. ........................................ 435/29; 435/34; 436/84; 436/164; 436/169; 436/170; 430/223; 430/224; 430/225; 556/138; 556/140; 556/146; 556/148
[58] Field of Search ................. 435/4, 29, 34; 436/84, 436/164, 169, 170, 903, 904; 422/55-57; 430/223-225; 260/396 R, 397.6; 556/138, 140, 146, 148

[56] References Cited

U.S. PATENT DOCUMENTS

| | | | |
|---|---|---|---|
| 3,926,732 | 12/1975 | Anders et al. | 195/103.5 |
| 3,928,139 | 12/1975 | Dorn | 435/34 |
| 4,042,335 | 8/1977 | Clement | 422/56 |
| 4,045,221 | 7/1977 | DoMinh | 430/223 |
| 4,046,513 | 9/1977 | Johnson | 23/253 |
| 4,144,306 | 3/1979 | Figueras | 422/56 |
| 4,195,998 | 4/1980 | Adin et al. | 430/156 |
| 4,215,995 | 8/1980 | Turk et al. | 23/230 |
| 4,258,001 | 3/1981 | Pierce et al. | 422/56 |
| 4,376,820 | 3/1983 | Giannini et al. | 435/4 |
| 4,419,435 | 12/1983 | Reczek et al. | 430/223 |
| 4,610,961 | 9/1986 | Guardino et al. | 435/34 |
| 4,701,420 | 10/1987 | Thunberg et al. | 436/94 |
| 4,746,607 | 5/1988 | Mura et al. | 422/56 X |
| 4,755,472 | 7/1988 | Ismail et al. | 435/28 |

FOREIGN PATENT DOCUMENTS

| | | | |
|---|---|---|---|
| 0255087 | 2/1988 | European Pat. Off. | 435/4 |
| 1262660 | 11/1986 | Japan | 435/4 |
| 2195559 | 8/1987 | Japan | 435/4 |
| 8604681 | 8/1986 | World Int. Prop. O. | 435/4 |

Primary Examiner—Esther L. Kepplinger
Assistant Examiner—Carol A. Spiegel
Attorney, Agent, or Firm—Doreen M. Wells

[57] ABSTRACT

Water soluble polymers are useful in combination with cobalt(III) redox reagents. When incorporated with the polymers, the cobalt(III) reagents exhibit improved sensitivity compared to fresh solutions of the reagents. In preferred embodiments, the cobalt(III) reagents are coated on a support using the water soluble polymer as a binder. Small areas of the coated support are then cut out and placed in a buffer solution to provide a working reagent solution. The solution is particularly useful in the testing of urine for significant bacteriuria.

10 Claims, No Drawings

5,171,669

COBALT(III) REAGENTS IN COMBINATION WITH WATER SOLUBLE POLYMERS

CROSS-REFERENCE TO RELATED APPLICATIONS

Reference is made to the following copending and commonly assigned application: U.S. Ser. No. 890,051 filed Jul. 28, 1986 by E. R. Schmittou entitled COBALT CONTAINING REAGENTS AND METHODS FOR THE DETERMINATION OF ANALYTES IN AQUEOUS FLUIDS.

FIELD OF THE INVENTION

The present invention is related to clinical chemistry and more particularly to compositions containing redox reagents which are useful in the determination of reductants in liquid samples.

BACKGROUND OF THE INVENTION

Chemical analysis of liquids, such as water, milk and biological fluids is often desirable or necessary for health maintenance and diagnostic treatment. Various compositions and elements to facilitate such analyses are known. Such compositions and elements generally include a reagent composition for determining a substance under analysis, termed an analyte herein. The analyte can be a biological organism or a chemical substance. This reagent composition, upon interaction with the analyte, provides a detectable change (e.g. dye formation).

Recently, much work has been directed to developing compositions and elements which are useful for rapid and highly quantitative diagnostic or clinical analysis of biological fluids such as whole blood, serum, plasma, urine and the like.

For the rapid and effective diagnosis and treatment of infectious diseases, it is desirable to be able to detect the bacteria causing the disease as rapidly as possible. Infections of the urinary tract are among the most common bacterial diseases, second in frequency only to infections of the respiratory tract. In fact, in many hospitals, urinary tract infections are the most common form of nosocomial infections, often following the use of catheters and various surgical procedures. Most urinary tract infections (UTI) result from ascending infection by microorganisms introduced through the urethra and vary in severity from an unsuspected infection to a condition of severe systemic disease. Such infections are usually associated with bacterial counts of 100,000 ($10^5$) or more organisms per ml of urine, a condition referred to as significant bacteriuria. Under normal conditions, urine is sterile, although contamination from the external genitalia may contribute up to 1,000 ($10^3$) organisms per ml in properly collected and transported specimens.

Significant bacteriuria may be present in a number of pathological conditions involving microbial invasion of any of the tissues of the urinary tract, or may result from simple bacterial multiplication in the urine without tissue invasion. The infection may involve a single site such as the urethra, prostate, bladder, or kidney, although frequently it involves more than one site. Infection restricted to the urine may present itself as asymptomatic bacteriuria, i.e., a condition which manifests no overt signs or symptoms of infection. Early treatment of this condition can prevent the development of more serious conditions, e.g., pyelonephritis (inflammation of the kidney and the renal pelvis). The rapid detection of bacteria by a reliable method would therefore facilitate an early and specific diagnosis.

Further, in order to insure that a prescribed antibiotic is in fact effective in treating an infection, repeated tests during therapy are required. The need for simple, rapid bacteriuria tests is thus clear. Moreover, in view of the frequent unsuspected asymptomatic occurrences of UTI among children, pregnant women, diabetics and geriatric populations, diagnosis of which may require collection and testing of several specimens, bacteriuria tests must be sufficiently simple and economical to permit routine performance. Again, this illustrates the need for a rapid and inexpensive bacteriuria detection method.

A significant advance in the art was the development of cobalt(III) reagents for the determination of significant bacteriuria. This development is the subject of the related application of Schmittou cited above. These reagents comprise a water soluble cobalt(III) complex and a water soluble metallizable dye. The reagents can also contain an electron transfer agent and, when living cells are to be detected, a carbon source. While these reagents are more sensitive than most previous reagents used for this purpose, still further improvements in sensitivity were sought.

SUMMARY OF THE INVENTION

In accordance with the present invention there is provided a reagent composition for the detection of an analyte in an aqueous sample which comprises:

(1) a water soluble cobalt(III) complex which is capable of being reduced to a water soluble cobalt(II) complex by said analyte and, (2) a water soluble dye which is capable of being metallized by said cobalt(II) complex to form a water soluble cobalt(II) complex of the metallizable dye, wherein said cobalt(II) complex of the metallizable dye is capable of reacting with said cobalt(III) complex to produce a cobalt(III) complex of the metallizable dye and the cobalt(II) complex; and (3) a water soluble polymer.

In accordance with the present invention there is also provided an element that comprises a support having coated thereon the described reagent composition. In preferred embodiments, the water soluble dye is coated on one side of the support in a water soluble polymer and the remainder of the reagents are coated on the other side of the support.

There is also provided a method for using the described reagents.

DETAILED DESCRIPTION OF THE INVENTION

Improved sensitivity of the cobalt(III) containing reagents is achieved if they are combined with a water soluble polymer. The reason for the increased sensitivity is not understood. Comparisons of the reagents in fresh solution with the reagents and water soluble polymers are presented in the examples.

Any water soluble polymer can be used in the practice of the present invention. By water soluble, we mean that a water solution that is at least 1% by weight in the polymer can be formed. Useful polymers include natural polymers such as polysaccharides, polypeptides such as proteins and polynucleotides. Modified natural polymers are also useful including for example, water soluble derivatives of cellulose.

From a practical point of view, synthetic polymers are preferred. Reference is made to *Water Soluble Synthetic Polymers: Properties and Behavior*, Philip Molyneux, CRC Press 1983 for a description of useful synthetic polymers.

While any water soluble polymer will provide improved results with cobalt(III) reagents, polymers which include acrylamide, vinylpyrrolidone, acrylate or alcohol groups are particularly preferred.

Useful polymers (ratios by weight) include:
poly(acrylamide-co-N-vinyl-2-pyrrolidone) (50:50)
polyacrylamide
poly(acrylamide-co-N-vinyl-2-pyrrolidone) (90:10)
poly(N-vinyl-2-pyrrolidone)
poly(acrylamide-co-acrylic acid) (90:10)
poly(2-hydroxyethylacrylate)
polyvinylalcohol The currently preferred polymer is poly(acrylamide-co-N-vinyl-2-pyrrolidone) (90:10)

The reagent compositions of the present invention can take a variety of forms. For example, the cobalt(III) reagents can be dissolved in a solution along with the polymer of choice and then dried to form a powder or mass of the composition. In the preferred form, the composition is coated on a suitable support using the polymer as a binder. This provides a convenient method of providing an accurately measured amount of the desired reagent. In use, a sample of a coated element of known area is placed in a suitable container to which a known volume of liquid is added. The reagents and the polymer dissolve into the liquid forming a reagent solution. The sample to be tested is then added to this reagent solution and any optical density change that results is measured.

In one embodiment, the cobalt reagents can all be coated on one side of a support. In other embodiments reagents can be separated and coated on separate supports.

In a preferred embodiment, the components of the cobalt(III) reagents can be separated and coated on opposite sides of the same support. For example, if stored together, some cobalt(III) reagents might react with the metallizable dye. This storage problem can be overcome by coating the metallizable dye on one side of the support in a water soluble polymer and the remainder of the reagents on the other side of the support in the same or a different water soluble polymer.

When used in the coated manner described above, the coverage of the various components can vary widely. The preferred ratio of cobalt(III) reagents to water soluble polymer is between about 1:10 and 1:1. (weight ratio based on the weight of cobalt(III)). Similar ratios are used with uncoated reagents.

The support on which the composition of the invention is coated is not critical. Conventional supports such as paper and polymeric films can be used. A preferred support is poly(ethylene terephthalate).

The compositions of the present invention include cobalt(III) complex containing reagents. Cobalt(III) is a trivalent metal that typically has a coordination number of six. An extremely wide variety of ligands are known to coordinate to cobalt(III). If the ligands are selected so that they contain a negative charge, a valence can be satisfied by the ligand. Conversely, if the ligand is electrically neutral, the valence must be satisfied by a non-coordinated counter-ion and a salt is formed. For use in the present invention, water soluble complexes are required. The cobalt(III) complex salts, being more water soluble, are preferred.

Useful neutral ligands for forming Co(III) complexes include: ammonia; aliphatic amines, such as ethylenediamine, propylenediamine, diethylenetriamine; substituted or unsubstituted aromatic amines, such as aniline, 2-aminoethylaniline, 2,2'-bisaniline; substituted or unsubstituted heterocyclic amines, such as pyridine, 2,2'-bipyridine, 2-(aminomethyl)pyridine, 4,4'-dimethyl-2,2'-bipyridine, 2,2',2"-terpyridine, morpholine, pyrimidine, pyridazine, 2,2'-bipyrazine, quinoline, isoquinoline, acridine, thiazole, imidazole, triazine, 1,10-phenanthroline, 5-nitrophenanthroline, 2,2'-bipyrimidine, 2,2'-diimidazole; and oxygen donor ligands, e.g. amides such as N,N-dimethylformamide and water. Any anion can be used as the counter ion. For convenience, halide ions are preferred such as chloride, bromide and iodide. Other useful counter anions include, for example, azide, thiocyanate, tetrafluoroborate, nitrate, perchlorate, hexafluorophosphate, sulfate, carbonate, sulfonate and carboxylate ions.

Anionic ligands may also coordinate with cobalt(III) provided the charge on cobalt(III) is not completely neutralized by the ligands, so that the complex is a salt and therefore water soluble. Useful anionic ligands include halide, i.e., chloride, bromide, iodide or fluoride, azide, thiocyanate, nitrite, carbonate, carboxylate, sulfonate, oxalate and 2,4-pentanedionate ions.

The presently preferred cobalt complex is [Co(ethylene diamine)$_2$(2,2'-bipyridine)]Cl$_3$.

The other component that is used in the cobalt(III) containing reagent is a water soluble metallizable dye. A very wide variety of dyes that are capable of coordinating with a cobalt(II) and (III) ion are useful. The dyes must be water soluble. Many of the specific dyes listed in the references below are not water soluble but can be easily made so by the incorporation of a suitable solubilizing group in the dye molecule by conventional methods. Conventional solubilizing groups such as carboxylic acid, sulfonic acid and sulfate groups are useful.

Preferred dyes are also tridentate ligands for cobalt. Tridentate ligands form more stable complexes and therefore can more easily displace ligands from the cobalt(II) complex.

With these criteria in mind, useful dyes and dye classes are disclosed in U.S. Pat. Nos. 4,396,546; 4,273,708; 4,272,434; 4,024,993; 4,147,544 and 4,419,435.

The preferred dyes are: 2-[(3-methyl-2-pyridyl)azo]-1-naphthol-4-sulfonic acid, monoammonium salt; 2-[(5-carboxy-2-pyridyl)azo]-1-naphthol-4-sulfonic acid, diammonium salt; and 2-[(3-methyl-5-sulfo-2-pyridyl)azo]-1-naphthol-4-sulfonic acid, diammonium salt.

The composition of this invention optionally, but preferably, includes an electron transfer agent (identified herein as ETA) which can transfer electrons from the reductant to the cobalt(III) complex. In general, it is desirable that the ETA has a potential which is more positive than that of the reductant and less positive than that of the cobalt(III) complex.

ETA compounds useful in the practice of this invention include phenazine methosulfate, phenazine ethosulfate, and similar compounds, and substituted benzoquinones and naphthoquinones such as those described in copending and commonly assigned U.S. Pat. No. 4,746,607 issued May 24, 1988. Combinations of different ETA compounds can be used if desired. The preferred ETAs are trimethyl-1,4-benzoquinone, 4,5-dimethoxy-1,2-benzoquinone and 2,3-dimethoxy-5-methyl-1,4-benzoquinone.

The composition of the present invention can be dissolved in a buffer solution. Useful buffers include those which will maintain the pH of the composition at 9 or less, and preferably from about 6.5 to about 8. Representative buffers include phosphates, borates, N-2-hydroxy-ethylpiperazine-N'-2-ethane sulfonic acid, and other buffers known in the art, e.g. those described by Good et al in *Biochem.*, 5, p. 467 (1966) and *Anal. Biochem.*, 104, 300 (1980).

The compositions of this invention are useful for analytical determination (i.e. quantitative, semi-quantitative or qualitative detection) of aqueous or non aqueous liquids, e.g. biological fluids, manufacturing processes, wastewater, food stuffs, etc. Determinations can be made of various analytes, including living cells (e.g. bacteria, yeast, fungi, etc.), enzymes (e.g. lipase, glucose oxidase, lactate oxidase, creatine kinase, α-glycerophosphate oxidase, lactate dehydrogenase, alanine aminotransferase, aspartate aminotransferase and other NADH-based or peroxidase-based assays which include dehydrogenase or reductase enzymes), biological or chemical reductants other than living cells which will reduce the ETA (e.g. ascorbate, cysteine, glutathione, etc.), metabolizable substances (e.g. glucose, lactic acid, triglycerides, cholesterol, etc.), immunoreactants (e.g. antigens, antibodies, haptens, etc.), and other determinations made via a single reaction or sequence of reactions which brings about reduction of the reducible compound and release of a detectable species.

The compositions of this invention are particularly useful in detecting or quantifying living cells in biological samples. Although any biological sample suspected of having living cells therein (e.g. food, tissue, ground water, cooling water, pharmaceutical products, sewage, etc.) can be analyzed for bacteria, yeast, fungi, etc. by this invention, the invention is particularly useful for bacterial detection in aqueous liquids, such as human and animal fluids (e.g. urine, cerebral spinal fluid, blood and the like as well as stool secretions) and suspensions of human or animal tissue. The practice of this invention is particularly important for detection of urinary tract infections in urine (diluted or undiluted).

The detection of living cells, and particularly of bacterial cells, is often carried out in the presence of a nutrient for those cells although its presence is not essential. Any nutrient media can be used which contains useful carbon, and optionally nitrogen, sources. Conventional nutrient mediums having proper components and pH are well known in the art. Particularly useful nutrients are readily metabolizable carbon sources, such as simple sugars (glucose, sucrose, raffinose, maltose, lactose, galactose, fructose, etc.), glycols (e.g. glycerol, sorbitol, etc.), carboxylic acids (e.g. acetic acid, lactic acid, citric acid, etc. or salts thereof) starch, tryptose and the like. Particularly useful nutrients are glucose or tryptose, alone or in combination.

In a preferred embodiment in solution, there is provided a method for the determination of cells in a sample, said method comprising the steps of:

1) separating the cells from the sample,
2) washing the separated cells with:
   a) an iron chelate solution and
   b) a non-ionic surfactant solution and
3) contacting the washed cells with a reducible composition (the cobalt(III) reagents of the invention) so as to produce a detectable change in the presence of the cells.

A wide variety of iron chelates are useful in this preferred embodiment. The chelate can be made by simply mixing an iron salt with a suitable ligand, many of which are known. Useful iron chelates include iron(III) chelates of the following ligands:

(a) Ethylenedinitrilotetraacetic acid
(b) Nitrilotriacetic acid
(c) Diethylenetriaminepentaacetic acid
(d) 1,3-Diamino-2-hydroxypropane-N,N,N',N'-tetraacetic acid
(e) 1,2-Diaminopropane-N,N,N',N'-tetraacetic acid
(f) Ethylenediamine-N,N'-diacetic acid
(g) Iminodiacetic acid
(h) N-Methyliminodiacetic acid
(i) trans-1,2-Diaminocyclohexane-N,N,N',N'-tetraacetic acid
(j) 1,3-Diaminopropane-N,N,N',N'-tetraacetic acid The currently preferred chelates are a, b, g and h.

In addition to the iron chelate, the cells are also washed with a solution of non-ionic surfactant. The iron chelate and the surfactant can be in the same solution or in separate solutions. Where the cells are separated from the sample by filtration, the iron chelate and the surfactant can be in the filter material in which case the wash solution is made in situ.

Useful non-ionic surfactants include octylphenoxypolyethoxy ethanols commercially available from Rohm and Haas Company under the TRITON TM (e.g. X-100. 102, 165 and 305); p-nonylphenoxypolyethoxy ethanols commercially available from Olin Mathieson Co.; polyethyleneglycol ethers of alcohols available from Union Carbide Co. under the trade name TERGITOL (e.g. 15-S-7 and 15-S-9); polyoxyethylene compounds commercially available from ICI Americas under the trade name TWEEN (e.g. 20, 80); and natural non-ionic surfactants such as deoxycholate. Currently preferred nonionic surfactants are TRITON X-100 TM, TRITON X-405 TM, TWEEN 20 and TWEEN 80.

The following examples are presented for a further understanding of the invention.

The following materials were used in the examples:

Cell suspension: *Escherichia coli* cells (American Type Culture Collection No. 25922) were grown in brain heart infusion medium (Difco Labs) at 37° C. without shaking. Forty milliliters of cells that were grown overnight were harvested by centrifugation to form a pellet of cells. The pellet was resuspended in 25 mL of 0.05M phosphate buffer (pH 7.5) and the resulting suspension was recentrifuged. The washed pellet was suspended in 25 mL of buffer, and an aliquot was diluted with the same buffer to obtain an absorbance of 0.833 at 620 nm, measured against a buffer blank. An absorbance of 0.833 has been determined to correspond to a cell concentration of $5 \times 10^8$ cells/mL. This solution was then diluted 1 to 100 to yield a $5 \times 10^6$ *E. coli*/mL stock suspension.

Dye 1 = 2-[(5-carboxy-2-pyridyl)azo]-1-naphthol-4-sulfonic acid, diammonium salt Dye 2 = 2-[(3-methyl-2-pyridyl-5-sulfo)azo]-1-naphthol-4-sulfonic acid, diammonium salt Cobalt Complex = [Co(ethylenediamine)$_2$(2,2'-bipyridine)]Cl$_3$ Electron Transfer Agent (ETA) = 2,3-dimethoxy-5-methyl-1,4-benzoquinone.

Unless otherwise noted, all solutions were prepared with filtered distilled water.

EXAMPLE 1

Determination of *E. coli*: This example comprises a fresh solution versus a coated element wherein the reagents are coated in separate elements. Poly(ethylene terephthalate) was used as the support.

The first coating contained Dye 1 (1.1 g/m$^2$); ZONYL FSN TM (0.22 g/m$^2$) (coating aid surfactant from DuPont) and poly(acrylamide-co-N-vinylpyrrolidone), 90:10 (1.1 g/m$^2$).

The second coating contained cobalt complex (11 g/m$^2$); ZONYL FSN TM (0.22 g/m$^2$); glucose (8 g/m$^2$); ETA (0.89 g/m$^2$); and poly(acrylamide-co-N-vinylpyrrolidone) 90:10 (1.1 g/m$^2$).

Portions of each of these coatings (1 cm$^2$) were added to solutions containing 2.94 mL of potassium phosphate (KP) buffer, 0.05M, pH 7.0 and 60 μL of the *E. coli* cell suspension. For background controls, identical portions were added to solutions without cells.

Fresh solution controls contained 2.34 mL KP buffer, 0.05M, pH 6.8; 60 μL *E. coli* cell suspension in KP buffer; 25 μL of a 10% solution of glucose; 500 μL of a solution of Cobalt Complex, 28 mg/10 mL of KP buffer; 50 μL Dye 1, 30.5 mg/10 mL of KP buffer; and 25 μL of a 0.01M solution of ETA in methanol. A background control contained all of the reagents except the cell suspension.

The solutions were maintained at 37° C. and optical densities were then read at 610 nm. Results are shown in the Table 1 as the change in optical density (ΔOD) after the specified time, corrected for background.

TABLE 1

| | Determination of *E. coli* ΔOD, 610 nm | |
|---|---|---|
| | 1 × 10$^6$ cells/mL ΔOD 16 min | 1 × 10$^5$ cells/mL ΔOD 30 min |
| Control | 0.379 | 0.126 |
| Example 1 | 0.949 | 0.324 |

EXAMPLE 2

Determination of *E. coli*: This example compares fresh solution versus a coated element wherein all the reagents are coated on one side of the same element. It also illustrates the excellent stability of a coating that was kept at 0° C. for one year prior to testing.

The coating contained Dye 2 (1.1 g/m$^2$); Cobalt Complex (11 g/m$^2$); ZONYL FSN TM (0.2 g/m$^2$); glucose (2.2 g/m$^2$); ETA (0.8 g/m$^2$); and poly(acrylamide-co-N-vinyl-2-pyrrolidone), 90:10 (1.1 g/m$^2$. Portions of this coating (1 cm$^2$) were added to solutions containing 2.94 mL of KP buffer, 0.05M, pH 7.0 and 60 μL of *E. coli* cells. For background control, identical portions were added to solutions without cells.

Fresh solution controls contained 2.34 mL KP buffer, 0.05M, pH 6.8; 60 μL *E. coli* cell suspension; 25 μL glucose solution; 500 μL cobalt complex; 50 μL of Dye 2 solution, 3.57 mg/mL KP buffer; 25 μL ETA. A background control contained all reagents except the cell suspension.

The solutions were maintained at 37° C. and optical densities were then read at 610 nm. Results are shown in Table 2 as the change in optical density (ΔOD) after 30 minutes, background corrected, for fresh coatings and coatings kept at 0° C. for one year.

TABLE 2

| | Determination of *E. coli* ΔOD, 610 nm, 30 min, 37° C. | | | |
|---|---|---|---|---|
| | 1 × 10$^5$ cells/mL | | 1 × 10$^6$ cells/mL | |
| | Control | Test | Control | Test |
| Fresh Coating | 0.044 | 0.161 | 0.427 | 0.940 |
| Kept 1 year at 0° C. | 0.081 | 0.145 | 0.638 | 0.799 |

EXAMPLE 3

Determination of *E. coli*: This example compares a fresh solution versus a coated element wherein the reagents are coated on opposite sides of a poly(ethylene terephthalate) support.

One side of the support had a layer containing Dye 1 (1.1 g/m$^2$); ZONYL FSN TM (0.22 g/m$^2$) and poly(acrylamide-co-N-vinyl-pyrrolidone), 90:10 (1.1 g/m$^2$). The layer on the other side contained Cobalt Complex (16.2 g/m$^2$); glucose (2.2 g/m$^2$); ZONYL FSN TM (0.22 g/m$^2$); ETA (0.8 g/m$^2$); and poly (acrylamide-co-N-vinyl-pyrrolidone); 90:10 (1.1 g/m$^2$).

A portion of the coating (1 cm$^2$) was added to a solution containing 2.94 mL KP buffer, 0.05M, pH 7.0 and 60 μL *E. coli* cell suspension. For background control, identical portions were placed in solutions without the cell suspension.

Fresh solution control contained 2.34 mL KP buffer, 0.05M, pH 6.8; 60 μL *E. coli* cell suspension; 25 μL glucose; 500 μL Cobalt Complex; 50 μL Dye 1; and 25 μL ETA. A background control contained all reagents except cells.

The solutions were maintained at 37° C. and optical densities were then read at 610 nm. Results are shown in Table 3 as the change in optical density (ΔOD) after 30 minutes, background corrected.

TABLE 3

| | Determination of *E. coli* |
|---|---|
| | 1 × 10$^5$ *E. coli* cells/mL |
| Solution Control | 0.093 |
| Test | 0.147 |

EXAMPLES 4–11

The following water soluble polymers were tested in compositions of the invention. Ratios are by weight.

P-1 poly(acrylamide-co-N-vinyl-2-pyrrolidone) (90:10)
P-2 polyacrylamide
P-3 same as P-1, weight ratio (50:50)
P-4 poly(N-vinyl-2-pyrrolidone)
P-5 poly(acrylamide-co-acrylic acid) (90:10)
P-6 poly(2-hydroxyethylacrylate)
P-7 polyvinylalcohol These polymers were coated onto poly(ethylene terephthalate) at a coverage of 1.1 g/m$^2$.

Portions (1.0 cm$^2$) of these coatings were added to a solution of the following reagents:

500 μL of cobalt complex, 4.14 mg/mL of potassium phosphate (KP) buffer, pH 7.0,
50 μL of dye 1, 3.05 mg/mL KP buffer, pH 7.0,
25 μL of ETA, 1.82 mg/mL methanol,
25 μL glucose, 10% solution in water, and
30 μL of *E. coli* cell suspension, 5×10$^7$ cells/mL in KP buffer, final cell conc, 5×10$^5$ cells/mL.

Additional KP buffer was added to yield a final volume of 3 mL.

A control solution contained all of the above reagents except polymer.

Optical densities (OD) were read at 610 nm at 37° C., and the differences in OD were determined after 30 minutes. Results are shown in the table as corrected densities (minus background).

TABLE 4

Assay for E. coli (5 × 10⁵ cells/mL)

| | Corrected ΔOD, 610 nm, 37° C. |
|---|---|
| Control (no polymer) | 0.981 |
| P-1 | 1.398 |
| P-2 | 1.535 |
| P-3 | 1.533 |
| P-4 | 1.132 |
| P-5 | 1.120 |
| P-6 | 1.364 |
| P-7 | 1.363 |

The invention has been described in detail with particular reference to preferred embodiments thereof, but it will be understood that variations and modifications can be effected within the spirit and scope of the invention.

What is claimed is:

1. A reagent composition for the detection of an analyte in an aqueous sample which comprises:
   (1) a water soluble cobalt(III) complex which is capable of being reduced to a water soluble cobalt(II) complex by said analyte and,
   (2) a water soluble dye which is capable of being metallized by said cobalt(II) complex to form a water soluble cobalt(II) complex of the metallizable dye, wherein said cobalt(II) complex of the metallizable dye is capable of reacting with said cobalt(III) complex to produce a cobalt(III) complex of the metallizable dye and the cobalt(II) complex; and
   (3) a water soluble polymer.

2. A reagent composition according to claim 1 wherein said water soluble polymer includes a repeating unit having a group selected from the group consisting of acrylamide, vinylpyrrolidone, acrylate and vinylalcohol.

3. A reagent composition according to claim 2 wherein said repeating unit is vinylpyrrolidone or acrylamide.

4. A reagent composition according to claim 3 wherein said water soluble polymer is poly(acrylamide-co-N-vinyl-2-pyrrolidone) (90:10 by weight).

5. A reagent composition according to claim 1 further comprising an electron transfer agent.

6. A reagent composition according to claim 5 wherein said electron transfer agent is a quinone.

7. A reagent composition according to claim 1 comprising
   (1) [Co(ethylenediamine)$_2$ (2,2'bipyridine)]Cl$_3$.
   (2) 2-[(5-carboxy-2-pyridyl)azo]-1-naphthol-4-sulfonic acid, diammonium salt
   (3) poly(acrylamide-co-N-vinyl-2-pyrrolidone) (90:10 by weight).

8. An element comprising a support having coated thereon a reagent composition according to claim 1.

9. An element according to claim 8 wherein the water soluble dye is coated on one side of the support and the remainder of the reagents are coated on the other side of the support.

10. A method for the determination of an analyte in a liquid comprising the steps of:
    (A) contacting a sample of said liquid with a reagent composition comprising:
       (1) a water soluble cobalt(III) complex which is capable of being reduced to a water soluble cobalt(II) complex by said analyte and,
       (2) a water soluble dye which is capable of being metallized by said cobalt(II) complex to form a water soluble cobalt(II) complex of the metallizable dye, wherein said cobalt(II) complex of the metallizable dye is capable of reacting with said cobalt(III) complex to produce a cobalt(III) complex of the metallizable dye and the cobalt(II) complex; and
       (3) a water soluble polymer so as to produce a detectable change in the presence of said analyte and
    (B) detecting said detectable change and relating said change to the amount of analyte in said liquid.

* * * * *